US00PP19584P2

(12) United States Plant Patent
van Kleinwee

(10) Patent No.: US PP19,584 P2
(45) Date of Patent: Dec. 23, 2008

(54) ***HELIOTROPIUM* PLANT NAMED 'HELIOBU'**

(50) Latin Name: *Heliotropium arborescens*
Varietal Denomination: Heliobu

(75) Inventor: Theodorus Cornelis Maria van Kleinwee, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 12/008,911

(22) Filed: Jan. 15, 2008

(51) Int. Cl.
*A01H 5/00* (2006.01)

(52) U.S. Cl. ..... Plt./438
(58) Field of Classification Search ..... Plt./438
See application file for complete search history.

*Primary Examiner*—Annette H Para
(74) *Attorney, Agent, or Firm*—S. Matthew Edwards

(57) ABSTRACT

A new *Heliotropium* plant named 'Heliobu' particularly distinguished by its dark green foliage, compact plant habit, its early flowering, its deep violet blue flower color, and very strong branching.

1 Drawing Sheet

Latin name of the genus and species of the plant claimed: *Heliotropium arborescens.*
Varietal denomination: 'Heliobu'.

BACKGROUND OF THE NEW PLANT

The present invention relates to a new and distinct cultivar of *Heliotropium* plant, botanically known as *Heliotropium* sp., and hereinafter referred to by the cultivar name 'Heliobu'.

The new *Heliotropium* is a product of a planned breeding program conducted in Enkhuizen, Netherlands. The new *Heliotropium* cultivar is early flowering and has a compact plant habit.

The new *Heliotropium* originates from an open pollination in July 2002 of a proprietary selection of *Heliotropium arborescens* identified as code number 'B0473-1', not patented, as the female, or seed parent. The male parent is unknown. The new *Heliotropium* was selected as a single plant from the resulting progeny of the open pollination in a controlled environment in Enkhuizen, Netherlands in May 2003.

Asexual reproduction of the new cultivar by terminal cuttings at Enkhuizen, Netherlands since August 2003, has shown that the unique features of this new *Heliotropium* are stable and reproduced true to type in successive generations.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Heliotropium.*

SUMMARY OF THE INVENTION

The following traits have been repeatedly observed and are determined to be the unique characteristics of 'Heliobu'. These characteristics in combination distinguish 'Heliobu' as a new and distinct cultivar:

1. Dark green foliage
2. Compact plant habit
3. Early flowering
4. Deep violet blue flower color
5. Very strong branching In side-by-side comparisons conducted in Enkhuizen, Netherlands, plants of the new *Heliotropium* differed from plants of the female parent selection in the following characteristics:

1. Plants of the new *Heliotropium* flower earlier than plants of the female parent selection.
2. Plants of the new *Heliotropium* are more branched than plants of the female parent selection.

TABLE 1

DIFFERENCES BETWEEN THE NEW CULTIVAR 'HELIOBU' AND A SIMILAR CULTIVAR

| | 'Heliobu' | 'Nagano' (Not patented) |
|---|---|---|
| Vigour | Medium to low | Very low |
| Floriferousness | Very floriferous | Medium floriferous |
| Branching | Very strong | Strong |

BOTANICAL DESCRIPTION OF THE PLANT

Plants used in the aforementioned photographs and for the following description were grown under conditions which closely approximate commercial production conditions during the spring and summer in a glass-covered greenhouse in Enkhuizen, Netherlands. Plants were grown in containers and were described approximately 20 weeks after planting rooted cuttings. During the production of the plants, day temperatures ranged from 20° to 30° C., night temperatures ranged from 10° to 15° C. In the following description, color references are made to The Royal Horticultural Society Colour Chart, 2001 Edition, except where general terms of ordinary dictionary significance are used.

The plant:

*Botanical classification.*—*Heliotropium* arborescens.

Parentage:

*Female parent.*—Proprietary selection 'B0473-1', not patented.

*Male parent.*—Unknown.

Propagation:

*Type.*—Terminal cuttings.

*Time to initiate roots.*—1 week.

*Time to develop roots.*—2 weeks.

*Root description.*—Fibrous.

*Rooting habit.*—Freely branching.

Plant description:

*Growth habit.*—Upright.

*Height* (*soil level to top of plant plane*).—20–30 cm.

*Diameter* (*area of spread*).—About 50 cm.

*Branching habit.*—Freely branching without pinching.

*Number of basal branches per plant.*—3–4.

*Number of lateral branches per plant.*—7–10.

The stem:

*Diameter.*—5–8 mm.

*Shape.*—Round.

*Length of stem length.*—Up to 30 cm.

*Lateral branch length.*—Up to 25 cm.

*Internode length.*—12–20 mm, depending on light intensity.

*Pubescence.*—Canescent.

*Color.*—Young stem: 144B. Old stem: Lighter than N199B, with anthocyanin.

The foliage:

*Arrangement.*—Alternate.

*Number of leaves.*—Up to 35.

*Shape of leaf blade.*—Elliptic to lanceolate.

*Fragrance.*—Light scent of hay.

*Leaf.*—Apex: Acute. Base: Shortly attenuate. Margin: Entire. Length: Up to 9 cm on mature plant. Width: Up to 4.5 cm. Texture: Puberulous — hirtellous. Color Upper side: 147A. Lower side: Young leaf 137B; old leaf 137C.

*Petiole.*—Length: 9–11 mm. Color: 144B. Diameter: About 2 mm. Texture: Densely pubescent with short, soft hairs.

*Venation.*—Shape: Pinnate. Color: 144B.

The inflorescence:

*Flowering season.*—From spring to end of fall.

*Type.*—Terminal compound cymene.

*Height.*—Up to 3 cm.

*Width at beginning of flowering.*—2–4 cm.

*Width at end of flowering.*—Up to 10 cm.

*Nr of open flowers per inflorescence.*—Up to 100.

*Fragrance.*—Strong.

*Lastingness of inflorescence on plant.*—4 weeks.

*Bud.*—Shape: Tubular. Length: About 4 mm. Diameter: About 1 mm. Color: 79A.

*Peduncle.*—Strength: Strong. Aspect: At an angle of 45° to the stem. Length: 1–3 cm. Diameter: About 2 mm. Texture: Pubescent. Color: 144A.

*Corolla.*—Shape: Funnel shaped, slightly rotate. Length: 8–10 mm. Width: About 8 mm. Nr of petals: 5, fused at base, forming a tube. Apex: Rounded. Margin: Entire. Texture upper and lower side: Smooth. Color Upper side: N87A. Lower side: 86B. Corolla tube Length: About 4 mm. Diameter at base: 1–1.5 mm. Diameter at tube opening: About 1 mm. Texture outer surface: Pubescent. Texture inner surface: Smooth. Color outer surface: N77A. Color inner surface: 151B.

*Sepals.*—Number: 5, fused at base. Shape: Deltoid. Length: About 3 mm. Width: About 1 mm. Apex: Acute. Margin: Entire. Texture: Densely pubescent with long soft hairs. Color: N187A.

Androecium.

Anther. —Color 149D. Length: 1–2 mm. Shape: Ligulate.

*Stamen.*—Number: 5, fused to tube. Length: About 0.3 mm.

*Pollen color.*—150D.

*Amount of pollen.*—Small.

Gynoecium:

*Pistil.*—Number: 1. Length: About 2 mm.

*Style.*—Length: About 0.3 mm. Color: 149D.

*Ovary.*—Number: 1 per pistil. Diameter: 0.5 mm. Length: 0.3 mm. Color: 149C.

*Stigma.*—Shape: Cordate. Color: 149C; apex 149D.

Seed development: Seed development has been observed on plants of the new *Heliotropium.*

*Length.*—1–1.5 mm.

*Diameter.*—About 1 mm.

*Color.*—151A.

*Shape.*—Obovate.

Disease resistance: No disease/pest resistance has been observed to date.

Temperature tolerance: Plants of the new *Heliotropium* have been observed to be tolerant to temperatures ranging from 4° to 35° C.

What is claimed i:

1. A new and distinct variety of *Heliotropium* plant named 'Heliobu,' as substantially illustrated and described herein.

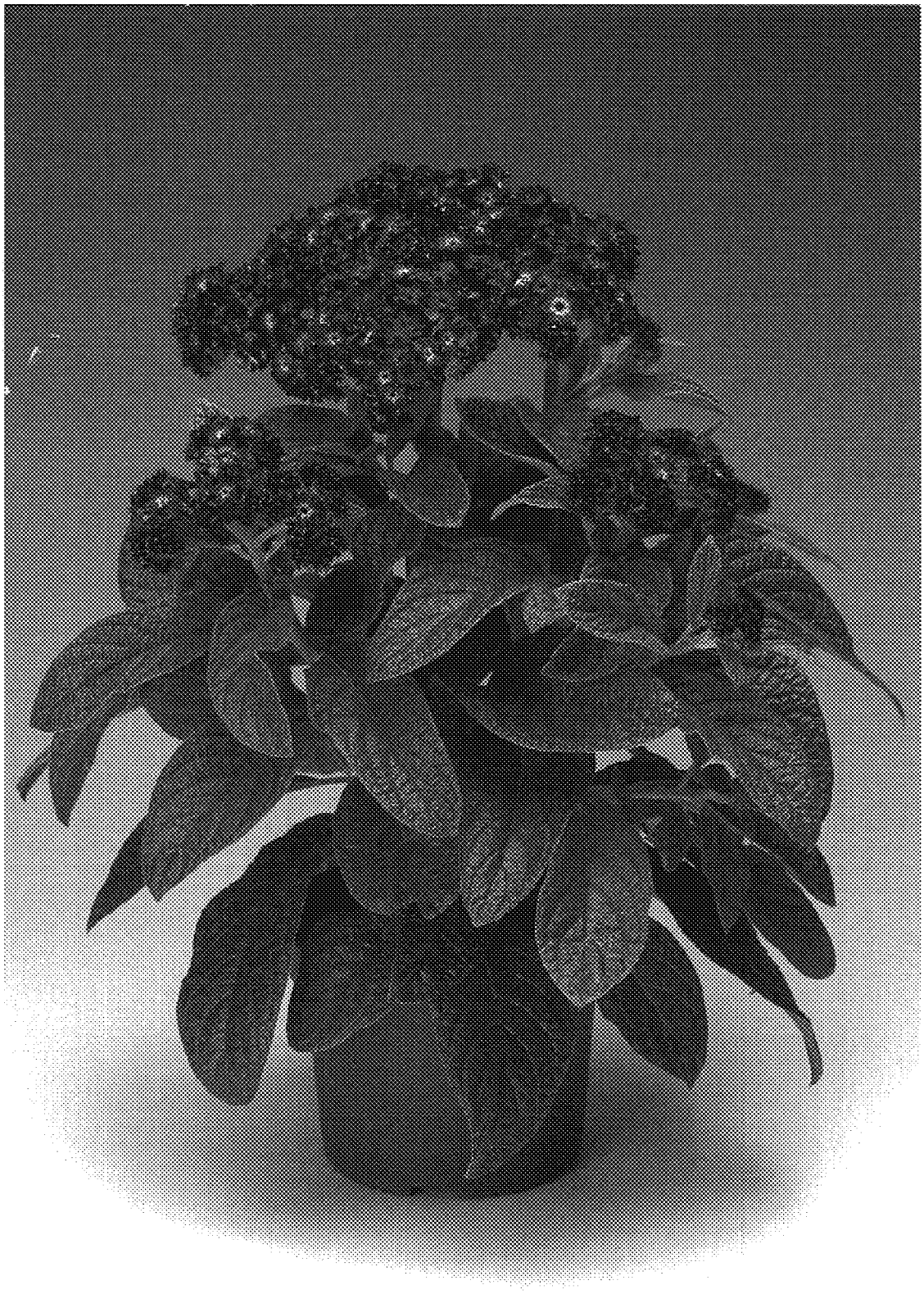

* * * * *